United States Patent
Grubb et al.

(10) Patent No.: US 6,319,912 B1
(45) Date of Patent: Nov. 20, 2001

(54) CYCLIC REGIMENS USING 2,1-BENZISOTHIAZOLINE 2,2-DIOXIDES

(75) Inventors: Gary S. Grubb, Newtown Square, PA (US); Lin Zhi, San Diego, CA (US); Todd K. Jones, Solana Beach, CA (US); James P. Edwards, San Diego, CA (US); Christopher M. Tegley, Thousand Oaks, CA (US); Mark A. Collins, Norristown; Valerie A. Mackner, Conshohocken, both of PA (US); Jay E. Wrobel, Lawrenceville, NJ (US)

(73) Assignees: American Home Products Corporation, Madison, NJ (US); Ligand Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/552,038

(22) Filed: Apr. 19, 2000

Related U.S. Application Data

(60) Provisional application No. 60/183,023, filed on May 4, 1999, now abandoned.

(51) Int. Cl.⁷ .......................... A61K 31/56; A61K 31/535
(52) U.S. Cl. .................. 514/171; 514/223.2; 514/222.5; 514/226.8; 514/228.2; 514/223.8
(58) Field of Search .................. 514/171, 223.2, 514/222.5, 226.8, 228.2, 223.8

(56) References Cited

U.S. PATENT DOCUMENTS

| | | |
|---|---|---|
| 3,635,964 | 1/1972 | Skorcz et al. .................. 260/247.1 |
| 3,917,592 | 11/1975 | Kobzina .................. 260/244 |
| 4,093,730 | 6/1978 | Butti .................. 424/270 |

(List continued on next page.)

FOREIGN PATENT DOCUMENTS

| | | |
|---|---|---|
| 3633861 | 4/1988 | (DE) . |
| 43 30 234 | 3/1995 | (DE) . |
| 43 44 463 | 6/1995 | (DE) . |
| 022317 | 1/1981 | (EP) . |
| 0 208 510 | 1/1987 | (EP) . |
| 311135 | 4/1989 | (EP) . |
| 385850 | 9/1990 | (EP) . |
| 483077 | 9/1991 | (EP) . |
| 454330 | 10/1991 | (EP) . |
| 0 535 529 | 9/1992 | (EP) . |
| 510235 | 10/1992 | (EP) . |
| 947 507 | 10/1999 | (EP) . |
| 978 279 | 2/2000 | (EP) . |
| 63112584 | 5/1988 | (JP) . |
| WO 86/03749 | 7/1986 | (WO) . |
| WO 91/04974 | 4/1991 | (WO) . |
| WO 91/06545 | 5/1991 | (WO) . |
| WO 93/12085 | 6/1993 | (WO) . |
| WO 94/14434 | 7/1994 | (WO) . |
| WO 94/29272 | 12/1994 | (WO) . |
| WO 95/11013 | 4/1995 | (WO) . |
| WO 95/20389 | 8/1995 | (WO) . |
| WO 95/20972 | 8/1995 | (WO) . |
| WO 95/33746 | 12/1995 | (WO) . |
| WO 96/15794 | 5/1996 | (WO) . |
| WO 96/19458 | 6/1996 | (WO) . |
| WO 96/19997 | 7/1996 | (WO) . |
| WO 97/13767 | 4/1997 | (WO) . |
| WO 97/49407 | 12/1997 | (WO) . |
| WO 98/14436 | 4/1998 | (WO) . |
| WO 98/27059 | 6/1998 | (WO) . |
| WO 98/55116 | 12/1998 | (WO) . |
| WO 99/10325 | 3/1999 | (WO) . |
| WO 99/11264 | 3/1999 | (WO) . |
| WO 99/15500 | 4/1999 | (WO) . |
| WO 99/44608 | 9/1999 | (WO) . |

OTHER PUBLICATIONS

Mamaev, V.P., et al., "Synthesis of 4H–Thieno [3,2–B] Pyrrol–5(6H)–One" Bulletin of the Academy of Sciences on the USSR. Division of Chemical Science, US, Consultants Bureau. New York. Vol. 9, pp. 1549–1553, 1966.

Derwent WPI Abstract, Chwalisz, K., et al. "Female Contraceptive Method Comprises Gestation Treatment with Intermittent Progesterone Antagonist Administration.", DE 4,330,234. (Mar., 1995).

Derwent WPI Abstract, Chwalisz, K., et al. "Contraceptive Pack for Implantation Inhibition—Contains Competitive Progesterone Antagonist and Gestagen for Sequential Oral Administration.", DE 4,344,463. (Jun., 1995).

Kolasa, K., et al., "Preliminary Pharmacological Studies of the Central Action of Phenyl and Piperidinomethyl Derivatives of 2–Benzoxazolone." *Chemical Abstracts*, vol. 99, No. 1, Abst. No. 157a, Jul. 4, 1983.

Meanwell N.A., et al., "Regiospecific Functionalization of 1,3–dihydro–2H–Benzimidazol–2–One and Structurally Related Cyclic Urea Derivatives" *J. Organic Chem.*, 60(6): 1565–82 (Mar. 24, 1995).

(List continued on next page.)

*Primary Examiner*—Minna Moezie
*Assistant Examiner*—San-ming Hui
(74) *Attorney, Agent, or Firm*—Howson and Howson

(57) ABSTRACT

This invention relates to cyclic combination therapies utilizing, in combination with a progestin, an estrogen, or both, progesterone receptor antagonists of the general structure:

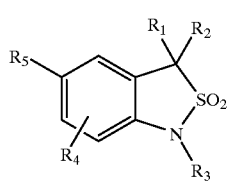

wherein the substituents are as defined herein, or pharmaceutically acceptable salt thereof.

10 Claims, No Drawings

U.S. PATENT DOCUMENTS

| | | | |
|---|---|---|---|
| 4,440,785 | 4/1984 | Walsh | 424/317 |
| 4,666,913 | 5/1987 | Kubla et al. | 514/259 |
| 4,670,566 | 6/1987 | Walsh | 548/485 |
| 4,721,721 | 1/1988 | Kuhla | 514/312 |
| 4,822,794 | 4/1989 | Spada | 514/230 |
| 4,831,027 | 5/1989 | Narr et al. | 514/212 |
| 4,853,473 | 8/1989 | Fischer et al. | 549/326 |
| 5,007,952 | 4/1991 | Kume et al. | 71/73 |
| 5,171,851 | 12/1992 | Kim et al. | 544/50 |
| 5,414,088 | 5/1995 | Von Der Saal et al. | 546/158 |
| 5,453,516 | 9/1995 | Fischer et al. | 548/543 |
| 5,475,020 | 12/1995 | Johnson et al. | 548/466 |
| 5,521,166 | 5/1996 | Grubb | 514/170 |
| 5,681,817 | 10/1997 | Hodgen et al. | 514/12 |
| 5,688,808 | 11/1997 | Jones et al. | 514/285 |
| 5,688,810 | 11/1997 | Jones et al. | 514/311 |
| 5,693,646 | 12/1997 | Jones et al. | 514/285 |
| 5,693,647 | 12/1997 | Jones et al. | 514/285 |
| 5,696,127 | 12/1997 | Jones et al. | 514/285 |
| 5,696,130 | 12/1997 | Jones et al. | 514/291 |
| 5,696,133 | 12/1997 | Pooley et al. | 514/314 |
| 5,719,136 | 2/1998 | Chwalisz et al. | 514/170 |
| 5,733,902 | 3/1998 | Schneider | 514/177 |
| 5,808,139 | 9/1998 | Pathirana | 560/138 |
| 5,874,430 | 2/1999 | Christ | 514/229.8 |
| 6,077,840 | 6/2000 | Kurihara | 514/232.8 |

OTHER PUBLICATIONS

Singh, B., et al., "An Efficient and Novel Synthesis of Fused Thiazol–2(3H)–ones" *Heterocycles*, 36(1): 133–134, p. 136, compounds 16a, 18a, Jan. 1993.

Vernin, G., et al., "Etude Dans la Serie des Radicaux Heterocycliques. Partie XV. Decomposition aprotique de 1' amino–6–ethyl–2–benzothiazole dans des substrats aromatiques et heteroaromatiques: preparation des mesityl–6– et furyl–6–ethyl–2–benzothiazoles, des sels quaternaires et des spiropyrannes correspondants" *Helvetica Chimica Acta*, 62(1/3):21–30 Jan. 24, 1979.

K. Horwitz et al., "Progestin, Progesterone Receptors, and Breast Cancer", "Hormones and Cancer", publisher: Birkhaeuser, Boston, Mass., ed. Vedeckis, pp. 283–306 (1996).

R.M. Evans, "The Steroid and Thyroid Hormone Receptor Superfamily", *Science*, 240:889 (May 13, 1988).

A. Ulmann et al., "Clinical Uses of Mifepristone (MFP)", *Ann. N.Y. Acad. Sci.*, 261:248 (Jun. 12, 1995).

R. Kekkonen et al., "Sequential Regiment of the Antiprogesterone RU486 and Synthetic Progestin for Contraception", *Fertility and Sterility*, 60(4):610 (Oct. 1993).

K. Horwitz et al., "Progestin, Progesterone Receptors, and Breast Cancer", "Horm. Cancer", publisher: Birkhaeuser, Boston, Mass., ed. Vedeckis, pp. 283–306 (1996) abstract only.

A. A. Murphy et al., "Regression of Uterine Leiomyomata in Response to the Antiprogesterone RU 486", *J. Clin. Endo. Metab.*, 76(2):513 (Feb. 1993).

L.M. Kettel et al., "Endocrine Responses to Long–Term Administration of the Antiprogesterone RU486 in Patients with Pelvic Endometriosis", *Fertility and Sterility*, 56(3):402 (Sep. 1991).

H. Michna et al., "Differentiation Therapy with Progesterone Antagonists", *Ann. N.Y. Acad. Sci.*, 761:224 (Jun. 1995).

L. Zhi et al., "5–Aryl–1,2–Dihydrochromeno[3,4–f]quinolines: A Novel Class of Nonsteroidal Human Progesterone Receptor Agonists", *J. Med. Chem.*, 41(3):291 (Oct. 22, 1998).

D. W. Combs et al., "Nonsteroidal Progesterone Receptor Ligands. 2. High–Affinity Ligands with Selectivity for Bone Cell Progesterone Receptors",*J. Med. Chem.*, 38:4880 (Dec. 8, 1995).

K. L. Perlman et al., "20–Oxopregnacalciferols: Vitamin D Compounds that Bind the Progesterone Receptor", *Tet. Letters*, 35(15):2295 (1994).

L. G. Hamann et al., "Synthesis and Biological Activity of Novel Nonsteroidal Progesterone Receptor Antagonists", *Ann. N.Y. Acad. Sci.*, 761:383 (Jun. 12, 1995).

R. H. K. Chen et al., "Synthesis and SAR of a Novel Series of Spirobenzothlzaepine Derivatives with Antiprogestin Activity", POI-37, $16^{th}$ Int. Cong. Het. Chem., Montana (1997).

B. Narr et al., "Preparation, Testing, and Formulation of Imidazobenzoxazinones as Cardiotonics", *Chemical Abstracts*, 109:22973 (1988).

R. J. Hartmann et al., "Effects of Brofoxine, A New Anxiolytic on Experimentally Induced Conflict in Rats", *Proc West. Pharmacol. Soc.*, 21:51–55 (1978).

B. Singh et al., "Novel cAMP PDE III Inhibitor; Imidazo [4,5–b]pyridin–2(3H)–ones and Thiazolo[4,5-b] pyridin–2(3H)–ones and Their Analogs", *J. Med. Chem.*, 37:248 (Jan. 21, 1994).

A. Andreani et al., "Potential Antitumor Agents XVII (1). Cytotoxic Agents from Indole Derivatives and Their Intermediates", *Acta. Pharm. Nord.*, 2(6):407 (1990).

Sakata et al., "Silver Halide Photographic Materials Useful for Platemaking", *Chemical Abstracts*, 123:301431 (1993).

P. Pflegel et al., "Polarografie con 7–Chlor–5–phenyl–2–thioxo–1H–2,3–dihydro–1,3,4–benzotriazepinen", *Pharmazie*, 37(10): 714–717 (1982).

E. I. Barengolts et al., "Progesterone Antagonist RU 486 Has Bone–Sparing Effects in Ovariectomized Rats", *Bone*, 17(1):21 (Jul. 1995).

E. V. Gromachevskaya et al., "Studies of 4H–3, 1–Benzoxazines", *Chem. Heterocycl. Cmpds.*, 33(10):1209–1214 (1997).

D. Chiarino et al., "2, 1–Benzisothiazoline 2, 3–Dioxide and Derivatives", *J. Heterocycl. Chem.*, 23(6):1645–1649 (Nov.– Dec. 1986).

A. Turck et al., "On the Metabolism of 3–Substituted and 3,6–Disubstituted Pyridazines", *Tetrahedron*, 49(3):599–606 (1993).

V. Kumar et al., "Synthesis of 7–Azaindole and 7–Azaoxindole Derivatives through a Palladium–Catalyzed Cross–Coupling Reaction", *J. Org. Chem.*, 57(25):6995–6998 (1992).

P. Canonne et al., "Spirocyclization of 1–(o–Aminophenyl) cycloalkanols and 1–(2'–Amino–3'–pyridinyl)cycloalkanols", *J. Heterocyclic Chem.*, 26:113 (Jan.–Feb. 1989).

M–C. Forest et al., "A Novel Class of Cardiotonic Agents; Synthesis and Biological Evaluation of 5–Substituted 3,6–Dihydrothiadiazin–2–ones with Cyclic AMP Phosphodiesterase Inhibiting and Myofibrillar Calcium Sensitizing Properties", *J. Med. Chem.*, 35:163–172 (Jan. 1992).

D. W. Combs et al., "Heteroatom Analogues of Bemoradan: Chemistry and Cardiotonic Activity of 1, 4–Benzothiazinylpyridazinones", *J. Med. Chem.*, 35:172–176 (Jan. 1992).

Kurihari et al., "Synthesis of (±)–PF1092A, B, and C; New Nonsteroidal Progesterone Receptor Ligands", *J. Antibodiotic*, 50(4):360 (Apr. 1997).

A. Kende et al., "Regioselective C–3 Alkylation of Oxindole Dianion", *Synth. Commun.* 12(1):1 (1982).

T. Tucker et al., "Synthesis of a Series of 4-(Arylethylnyl)–6–Chloro–4–Cyclopropyl–3, 4–dihydroquinazolin–2(1H)–ones as Novel Non–Nucleoside HIV–1 Reverse Transcriptase Inhibitors", *J. Med. Chem.*, 37:2347–2444 (Jul. 22, 1994).

J. P. Edwards et al., "5–Aryl–1,2–Dihydro–5H–Chromeno [3,4–f]Quinolines as Potent, Orally Active, Nonsteroidal Progesterone Receptor Agonists: The Effect of D–Ring Substituents", *J. Med. Chem.*, 41:303–310 (Jan. 29, 1998).

Derwent WPI abstract, "New Imidazo–Pyridine Derivatives—Useful as Platelet Agglutination Inhibitor, Antiallergic, Antiinflammatory Sedative, Cardiac, and Cardiovascular Vasodilators", JP 63112584, (May 1988).

Derwent WPI abstract, N. Brumagniez et al., "Benzimidazole and Azabenzimidazole(s)—Having Cardiotonic, Vasodilating, Anti–Hypertensive, Anti–Aggregation, and Anti–Ulcer Activity", EP 385850 (Sep. 1990).

Derwent WPI abstract, F. Arndt et al., "New Heterocycle substituted Benzo–Fused Azine and Azole Derivatives—Useful as Selective Herbicides for Pre or Post–Emergence Application", EP 311135 (Apr. 1989).

CYCLIC REGIMENS USING 2,1-BENZISOTHIAZOLINE 2,2-DIOXIDES

CROSS-REFERENCE TO RELATED APPLICATIONS

This application claims the benefit of the priority of U.S. Provisional Patent Application No. 60/183,023. Filing date May 4, 1999, abandoned.

BACKGROUND OF THE INVENTION

Intracellular receptors (IR) form a class of structurally related gene regulators known as "ligand dependent transcription factors" (R. M. Evans, *Science* 240, 889, 1988). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and protein encoded by that gene.

A compound that binds to an IR and mimics the action of the natural hormone is termed an agonist, whilst a compound that inhibits the effect of the hormone is an antagonist.

PR agonists (natural and synthetic) are known to play an important role in the health of women. PR agonists are used in birth control formulations, typically in the presence of an ER agonist. ER agonists are used to treat the symptoms of menopause, but have been associated with a proliferative effect on the uterus that can lead to an increased risk of uterine cancers. Co-administration of a PR agonist reduces or ablates that risk.

PR antagonists may also be used in contraception. In this context they may be administered alone (Ulmann et al, *Ann. N.Y. Acad. Sci.* 261, 248, 1995), in combination with a PR agonist (Kekkonen et al, *Fertility and Sterility* 60, 610, 1993) or in combination with a partial ER antagonist such as tamoxifen (WO 96/19997 A1 Jul. 4, 1996).

PR antagonists may also be useful for the treatment of hormone dependent breast cancers (Horwitz et al, *Horm. Cancer*, 283, pub: Birkhaeuser, Boston, Mass., ed. Vedeckis) as well as uterine and ovarian cancers. PR antagonists may also be useful for the treatment of non-malignant chronic conditions such as fibroids (Murphy et al, *J. Clin. Endo. Metab.* 76, 513, 1993) and endometriosis (Kettel et al, *Fertility and Sterility* 56, 402, 1991).

PR antagonists may also be useful in hormone replacement therapy for post menopausal patients in combination with a partial ER antagonist such as tamoxifen (U.S. Pat. No. 5,719,136).

PR antagonists, such as mifepristone and onapristone, have been shown to be effective in a model of hormone dependent prostate cancer, which may indicate their utility in the treatment of this condition in men (Michna et al, *Ann. N.Y. Acad. Sci.* 761, 224, 1995).

Jones et al (U.S. Pat. No. 5,688,810) described the PR antagonist dihydroquinoline A.

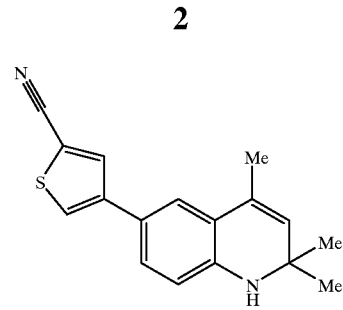

A

Jones et al described the enol ether B (U.S. Pat. No. 5,693,646) as a PR ligand.

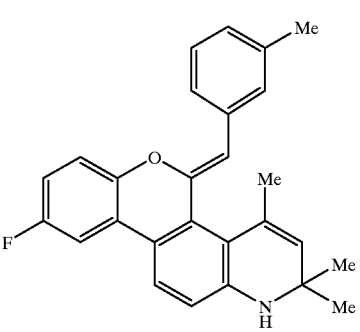

B

Jones et al described compound C (U.S. Pat. No. 5,696,127) as a PR ligand.

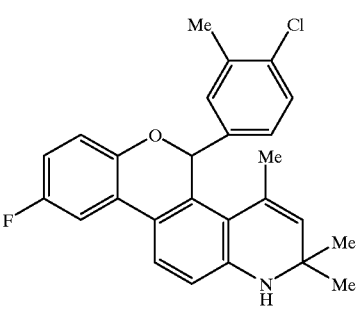

C

Zhi et al described lactones D, E and F as PR antagonists (*J. Med. Chem.* 41, 291, 1998).

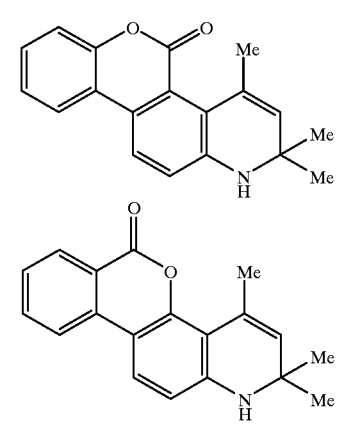

D

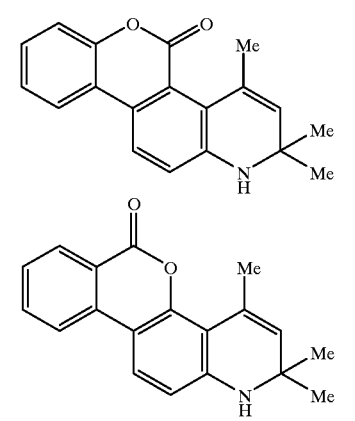

E

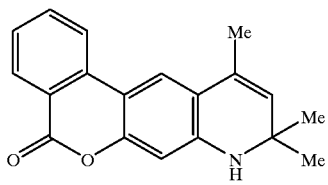

F

Zhi et al described the ether G as a PR antagonist (*J. Med. Chem.* 41, 291, 1998).

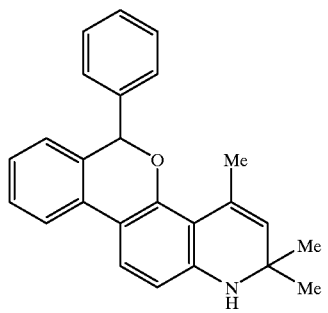

G

Combs et al disclosed the amide H as a ligand for the PR (*J. Med. Chem.* 38, 4880, 1995).

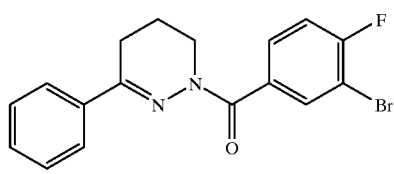

H

Perlman et al described the vitamin D analog I as a PR ligand (*Tetrahedron. Lett.* 35, 2295, 1994).

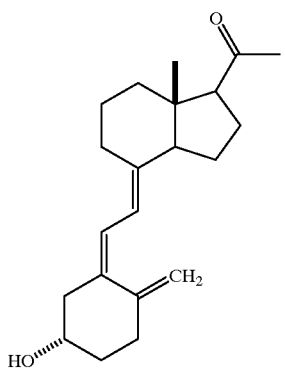

I

Hamann et al described the PR antagonist J (*Ann. N.Y. Acad. Sci.* 761, 383, 1995).

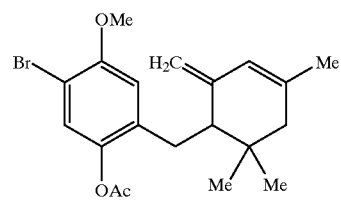

J

Chen et al described the PR antagonist K (Chen et al, POI-37, 16$^{th}$ Int. Cong. Het. Chem., Montana, 1997).

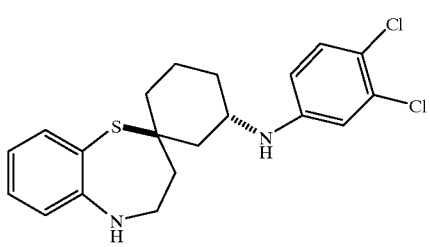

K

Kurihari et al described the PR ligand L (*J. Antibiotics* 50, 360, 1997).

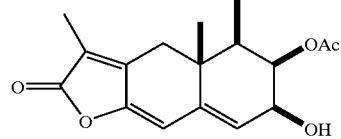

L

There are several examples of 2,1-benzisothiazoline 2,2-dioxides ('sultams') in the chemical and patent literature which contain no reference to progesterone activity, and do not carry the correct substitution pattern for PR modulator activity.

Chiarino et al described the preparation of the parent 2,1-benzisothiazoline 2,2-dioxide, i.e., M (and derivatives, e.g., N), that was used in the present invention (*J. Heterocycl. Chem.* 23(6), 1645–9, 1986).

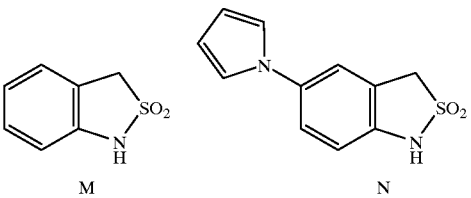

M              N

Skorcz et al described a series of 5-(2-morpholinyl)-2,1-benzisothiazolines, e.g., O, which are useful as central nervous depressants (U.S. Pat. No. 3,635,964).

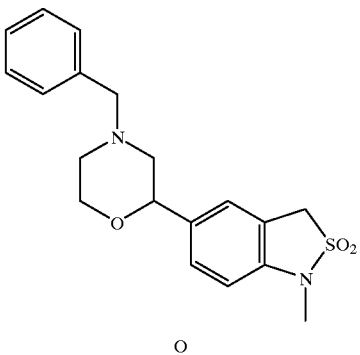

Kamireddy et al disclosed a series of cyclic sulfonamides, e.g., P and Q, useful for controlling undesired vegetation (WO 95/33746).

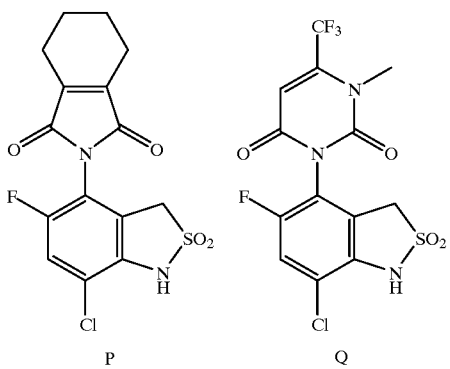

DESCRIPTION OF THE INVENTION

This invention provides combination therapies and dosing regimens utilizing antiprogestational agents in combination with one or more progestational agents. This invention further provides methods of treatment and dosing regimens further utilizing in combination with these antiprogestins and progestins, an estrogen, such as ethinyl estradiol.

These regimens and combinations may be administered to a mammal to induce contraception or for the treatment and/or prevention of secondary amenorrhea, dysfunctional bleeding, uterine leiomyomata, endometriosis; polycystic ovary syndrome, carcinomas and adenocarcinomas of the endometrium, ovary, breast, colon, prostate. Additional uses of the invention include stimulation of food intake. The uses herein for the treatment and/or prevention of the conditions or diseases described above includes the continuous administration or periodic discontinuation of administration of the invention to allow for minimization of effect dose or minimization of side effects or cyclic menstrual bleeding.

The use of this invention for contraception includes administration, preferably orally, to a female of child bearing age an antiprogestin in combination with an estrogen or progestin or both. These administration regimens are preferably carried out over 28 consecutive days, with a terminal portion of the cycle containing administration of no progestins, estrogens or anti-progestins.

The progestins of these combinations may be administered alone or in combination with an estrogen for the first 14 to 24 days of the cycle, the progestins being administered at a dosage range equal in progestational activity to about 35 µg to about 150 µg levonorgestrel per day, preferably equal in activity to from about 35 µg to about 100 µg levonorgestrel per day. An antiprogestin may then be administered alone or in combination with an estrogen for a period of 1 to 11 days to begin on any cycle day between day 14 and 24. The anti-progestin in these combinations may be administered at a dose of from about 2 µg to about 50 µg per day and the estrogen may be administered at a dose of from about 10 µg to about 35 µg per day. In an oral administration, a package or kit containing 28 tablets will include a placebo tablet on those days when the antiprogestin or progestin or estrogen is not administered.

In a preferred embodiment of this invention, the progestins of this invention may be administered alone or in combination with estrogen for the initial 18 to 21 days of a 28-day cycle, followed by administration of an antiprogestin, alone or in combination with an estrogen, for from 1 to 7 days.

The estrogen to be used in the combinations and formulations of this invention is preferably ethinyl estradiol.

Progestational agents useful with this invention include, but are not limited to, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, or (17-deacetyl)norgestimate. Among the preferred progestins for use in the combinations of this invention are levonorgestrel, gestodene and trimegestone.

Examples of orally administered regimens of this invention over a 28 day cycle include administration of a progestational agent solely for the first 21 days at a daily dose equal in progestational activity to from about 35 to about 100 µg of levonorgestrel. An antiprogestin compound of this invention may then be administered at a daily dose of from about 2 to 50 mg from day 22 to day 24, followed by no administration or administration of a placebo for days 25 to 28. It is most preferred that the daily dosages of each relevant active ingredient be incorporated into a combined, single daily dosage unit, totaling 28 daily units per 28-day cycle.

In another regimen, a progestational agent may be coadministered for the first 21 days at a daily dose equal in progestational activity to from about 35 to about 150 µg levonorgestrel, preferably equal in activity to from about 35 to about 100 µg levonorgestrel, with an estrogen, such as ethinyl estradiol, at a daily dose range of from about 10 to about 35 µg. This may be followed as described above with an antiprogestin administered at a daily dose of from about 2 to 50 mg from day 22 to day 24, followed by no administration or administration of a placebo for days 25 to 28.

Still another regimen within the scope of this invention will include coadministration from days 1 to 21 of a progestational agent, the progestational agent, preferably levonorgestrel, being administered at a daily dose equal in progestational activity to from about 35 to about 100 μg levonorgestrel, and an estrogen, such as ethinyl estradiol, at a daily dose range of from about 10 to about 35 μg. This will be followed on days 22 to 24 by coadministration of an antiprogestin (2 to 50 mg/day) and an estrogen, such as ethinyl estradiol, at a daily dose of from about 10 to about 35 μg. From day 25 to day 28, this regimen may be followed by no administration or administration of a placebo.

This invention also kits or packages of pharmaceutical formulations designed for use in the regimens described herein. These kits are preferably designed for daily oral administration over a 28-day cycle, preferably for one oral administration per day, and organized so as to indicate a single oral formulation or combination of oral formulations to be taken on each day of the 28-day cycle. Preferably each kit will include oral tablets to be taken on each the days specified, preferably one oral tablet will contain each of the combined daily dosages indicated.

According to the regimens described above, one 28-day kit may comprise:
 a) an initial phase of from 14 to 21 daily dosage units of a progestational agent equal in progestational activity to about 35 to about 150 μg levonorgestrel, preferably equal in progestational activity to about 35 to about 100 μg levonorgestrel;
 b) a second phase of from 1 to 11 daily dosage units of an antiprogestin compound of this invention, each daily dosage unit containing an antiprogestin compound at a daily dosage of from about 2 to 50 mg; and
 c) optionally, a third phase of an orally and pharmaceutically acceptable placebo for the remaining days of the cycle in which no antiprogestin, progestin or estrogen is administered.

A preferred embodiment of this kit may comprise:
 a) an initial phase of 21 daily dosage units of a progestational agent equal in progestational activity to about 35 to about 150 μg levonorgestrel, preferably equal in progestational activity to about 35 to about 100 μg levonorgestrel;
 b) a second phase of 3 daily dosage units for days 22 to 24 of an antiprogestin compound of this invention, each daily dosage unit containing an antiprogestin compound at a daily dosage of from about 2 to 50 mg; and
 c) optionally, a third phase of 4 daily units of an orally and pharmaceutically acceptable placebo for each of days 25 to 28.

Another 28-day cycle packaging regimen or kit of this invention comprises:
 a) a first phase of from 18 to 21 daily dosage units of a progestational agent equal in progestational activity to about 35 to about 150 μg levonorgestrel, preferably equal in activity to from about 35 to about 100 μg levonorgestrel, and, as an estrogen, ethinyl estradiol at a daily dose range of from about 10 to about 35 μg; and
 b) a second phase of from 1 to 7 daily dosage units of an antiprogestin of this invention at a daily dose of from about 2 to 50 mg; and
 c) optionally, an orally and pharmaceutically acceptable placebo for each of the remaining 0 to 9 days in the 28-day cycle in which no progestational agent, estrogen or antiprogestin is administered.

A preferred embodiment of the kit described above may comprise:
 a) a first phase of 21 daily dosage units of a progestational agent equal in progestational activity to about 35 to about 150 μg levonorgestrel, preferably equal in activity to from about 35 to about 100 μg levonorgestrel, and, as an estrogen, ethinyl estradiol at a daily dose range of from about 10 to about 35 μg; and
 b) a second phase of 3 daily dosage units for days 22 to 24 of an antiprogestin administered at a daily dose of from about 2 to 50 mg; and
 c) optionally, a third phase of 4 daily dose units of an orally and pharmaceutically acceptable placebo for each of days 25 to 28.

A further 28-day packaged regimen or kit of this invention comprises:
 a) a first phase of from 18 to 21 daily dosage units, each containing a progestational agent of this invention at a daily dose equal in progestational activity to about 35 to about 150 μg levonorgestrel, preferably equal in activity to from about 35 to about 100 μg levonorgestrel, and ethinyl estradiol at a daily dose range of from about 10 to about 35 μg;
 b) a second phase of from 1 to 7 daily dose units, each daily dose unit containing an antiprogestin of this invention at a concentration of from 2 to 50 mg; and ethinyl estradiol at a concentration of from about 10 to about 35 μg; and
 c) optionally, an orally and pharmaceutically acceptable placebo for each of the remaining 0 to 9 days in the 28-day cycle in which no progestational agent, estrogen or antiprogestin is administered.

A preferred embodiment of the package or kit just described comprises:
 a) a first phase of 21 daily dosage units, each containing a progestational agent of this invention at a daily dose equal in progestational activity to about 35 to about 150 μg levonorgestrel, preferably from about 35 to about 100 μg levonorgestrel, and ethinyl estradiol at a daily dose range of from about 10 to about 35 μg;
 b) a second phase of 3 daily dose units for days 22 to 24, each dose unit containing an antiprogestin of this invention at a concentration of from 2 to 50 mg; and ethinyl estradiol at a concentration of from about 10 to about 35 μg; and
 c) optionally, a third phase of 4 daily units of an orally and pharmaceutically acceptable placebo for each of days 25 to 28.

In each of the regimens and kits just described, it is preferred that the daily dosage of each pharmaceutically active component of the regimen remain fixed in each particular phase in which it is administered. It is also understood that the daily dose units described are to be administered in the order described, with the first phase followed in order by the second and third phases. To help facilitate compliance with each regimen, it is also preferred that the kits contain the placebo described for the final days of the cycle. It is further preferred that each package or kit comprise a pharmaceutically acceptable package having indicators for each day of the 28-day cycle, such as a labeled blister package or dial dispenser packages known in the art.

In this disclosure, the terms anti-progestational agents, anti-progestins and progesterone receptor antagonists are understood to be synonymous. Similarly, progestins, progestational agents and progesterone receptor agonists are understood to refer to compounds of the same activity.

These dosage regimens may be adjusted to provide the optimal therapeutic response. For example, several divided doses of each component may be administered daily or the dose may be proportionally increased or reduced as indicated by the exigencies of the therapeutic situation. In the descriptions herein, reference to a daily dosage unit may also include divided units that are administered over the course of each day of the cycle contemplated.

Antiprogestin compounds which may be used in the kits, methods and regimens herein are those of the Formula 1:

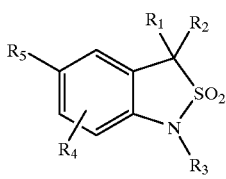

1 wherein $R_1$ and $R_2$ are each, independently, hydrogen, alky, substituted alkyl, hydroxy, alkoxy, substituted alkoxy, aryl, substituted aryl, heteroaryl, substituted heteroary, arylalkyl, heteroarylalkyl, and alkynyl; or $R_1$ and $R_2$ are taken together form a ring and together contain —$CH_2(CH_2)_nCH_2$—, —$CH_2CH_2CMe_2CH_2CH_2$—, —$O(CH_2)_pCH_2$—, $O(CH_2)_qO$—, —$CH_2CH_2OCH_2CH_2$—, —$CH_2CH_2NR_7CH_2CH_2$—; or $R_1$ and $R_2$ are a double bond, said double bond having two methyl groups bonded to the terminal end, having a cycloalkyl group bonded to the terminal end, having an oxygen bonded to the terminal end, or having a cycloether bonded to the terminal end;

$R_7$ is hydrogen or alkyl of 1–6 carbon atoms;

n=1–5;

p=1–4;

q=1–4;

$R^3$ is hydrogen, hydroxyl, $NH_2$, alkyl, substituted alkyl, alkenyl, alkynyl, substituted or, $COR^A$;

$R^A$ is hydrogen, alkyl, substituted alkyl, alkoxy, substituted alkoxy, aminoalkyl, or substituted aminoalkyl;

$R^4$ is hydrogen, halogen, —CN, —$NH_2$, alkyl, substituted alkyl, alkoxy, alkoxy, aminoalkyl, or substituted aminoalkyl;

$R^5$ is a trisubstituted phenyl ring having the structure,

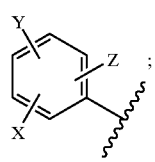

X is halogen, OH, —CN, alkyl, substituted alkyl, alkoxy, substituted alkoxy, thioalkyl, substituted thioalkyl, S(O)alkyl, S(O)$_2$alkyl, aminoalkyl, substituted aminoalkyl, —$NO_2$, perfluoroalkyl, 5 or 6 membered heterocyclic ring containing 1 to 3 heteroatoms, thioalkoxy, —$COR^B$, —$OCOR^B$, or —$NR^CCOR^B$;

$R^B$ is hydrogen, alkyl, substituted alkyl, aryl, substituted aryl, alkoxy, substituted alkoxy, aminoalkyl, or substituted aminoalkyl;

$R^C$ is hydrogen, alkyl, or substituted alkyl;

Y and Z are each, independently, hydrogen, halogen, —CN, —$NO_2$, alkoxy, alkyl, or thioalkyl; or $R^5$ is a five or six membered heteroaryl ring containing 1, 2, or 3 heteroatoms selected from the group consisting of O, S, SO, $SO_2$ and $NR^6$ with said ring carbons being optionally substituted with one or two substituents independently selected from the group consisting of hydrogen, halogen, CN, $NO_2$, alkyl, alkoxy, aminoalkyl, $COR^D$, and $NR^ECOR^D$;

$R^D$ is hydrogen, alkyl, substituted alkyl, aryl, substituted aryl, alkoxy, substituted alkoxy, aminoalkyl, or substituted aminoalkyl;

$R^E$ is hydrogen, alkyl, or substituted alkyl;

$R^6$ is hydrogen, alkyl, alkoxycarbonyl, or is absent when the nitrogen of $NR^6$ is bonded to a ring double bond;

or pharmaceutically acceptable salt thereof.

Preferred antiprogestin compounds for use with the methods and regimens this invention are those having the structure:

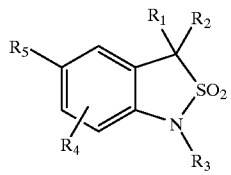

1 wherein $R_1$ and $R_2$ are taken together form a ring and together contain —$CH_2(CH_2)_nCH_2$—;

n=2–3;

$R^3$ is hydrogen;

$R^4$ is hydrogen;

$R^5$ is a trisubstituted phenyl ring having the structure,

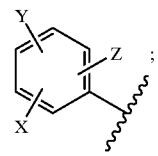

X is halogen, OH, —CN, alkyl, alkoxy, thioalkyl, substituted thioalkyl, S(O)alkyl, S(O)$_2$alkyl, aminoalkyl, substituted aminoalkyl, —$NO_2$, perfluoroalkyl, 5 or 6 membered heterocyclic ring containing 1 to 3 heteroatoms, or thioalkoxy;

Y and Z are each, independently, hydrogen, halogen, —CN, —$NO_2$, alkoxy, alkyl, or thioalkyl; or $R^5$ is a five or six membered heteroaryl ring containing 1, 2, or 3 heteroatoms selected from the group consisting of O, S, and $NR^6$ with said ring carbons being optionally substituted with one or two substituents independently selected from the group consisting of hydrogen, halogen, CN, $NO_2$, alkyl, or alkoxy;

$R^6$ is hydrogen, alkyl, alkoxycarbonyl, or is absent when the nitrogen of $NR^6$ is bonded to a ring double bond;

or pharmaceutically acceptable salt thereof.

More preferred compounds of this invention are those having the structure

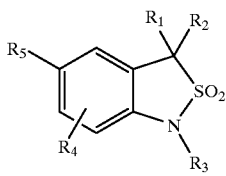

wherein
$R_1$ and $R_2$ are taken together form a ring and together contain —$CH_2(CH_2)_nCH_2$—;
n=2–3;
$R^3$ is hydrogen;
$R^4$ is hydrogen;
$R^5$ is a disubstituted phenyl ring having the structure,

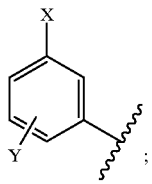

X is halogen, —CN, or —$NO_2$;
Y is hydrogen, halogen, —CN, —$NO_2$, alkoxy, alkyl, or thioalkyl; or
$R^5$ is a five or six membered heteroaryl ring containing a heteroatom selected from the group consisting of O, S, and $NR^6$ with said ring carbons being optionally substituted with one or two substituents independently selected from the group consisting of hydrogen, halogen, CN, or $NO_2$;
$R^6$ is hydrogen, or is absent when the nitrogen of $NR^6$ is bonded to a ring double bond;
or pharmaceutically acceptable salt thereof.

The antiprogestin compounds of this invention may contain an asymmetric carbon atom and some of the compounds of this invention may contain one or more asymmetric centers and may thus give rise to optical isomers and diastereoisomers. While shown without respect to stereochemistry in Formula 1, the present invention includes such optical isomers and diastereoisomers; as well as the racemic and resolved, enantiomerically pure R and S stereoisomers; as well as other mixtures of the R and S stereoisomers and pharmaceutically acceptable salts thereof.

The term "alkyl" is used herein to refer to both straight- and branched-chain saturated aliphatic hydrocarbon groups having 1 to 6 carbon atoms; "alkenyl" includes both straight- and branched-chain alkyl groups of 2 to 6 carbon atoms containing at least one carbon-carbon double bond; "alkynyl" group includes both straight- and branched-chain alkyl groups of 2 to 6 carbon atoms with at least one carbon-carbon triple bond.

The terms "substituted alkyl", "substituted alkenyl", and "substituted alkynyl" refer to alkyl, alkenyl, and alkynyl as containing one or more substituents from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, arylthio. These substituents may be attached to any carbon of alkyl, alkenyl, or alkynyl group provided that the attachment constitutes a stable chemical moiety.

The term "aryl" is used herein to refer to an aromatic system of 6 to 14 carbon atoms, which may be a single ring or multiple aromatic rings fused or linked together as such that at least one part of the fused or linked rings forms the conjugated aromatic system. Preferred aryl groups include phenyl, naphthyl, biphenyl, anthryl, tetrahydronaphthyl, phenanthryl groups.

The term "substituted aryl" refers to aryl substituted by one or more substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, or arylthio.

The term "heterocyclic" is used herein to describe a stable 4 to 14 membered monocyclic or multicyclic heterocyclic ring which is saturated, partially unsaturated, or unsaturated, and which consists of carbon atoms and from one to four heteroatoms selected from the group including N, O, and S atoms. The N and S atoms may be oxidized, as an N-oxide, sulfoxide, or sulfone. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "substituted heterocyclic" is used herein to describe a heterocyclic having one or more substituents selected from the group which includes halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, or arylthio. The term "thioalkyl" is used herein to refer to the SR group, where R is alkyl or substituted alkyl. The term "alkoxy" is used herein to refer to the OR group, where R is alkyl or substituted alkyl. The term "aryloxy" is used herein to refer to the OR group, where R is aryl or substituted aryl. The term "alkylcarbonyl" is used herein to refer to the RCO group, where R is alkyl or substituted alkyl. The term "alkylcarboxy" is used herein to refer to the COOR group, where R is alkyl or substituted alkyl. This term is also referred to as alkoxycarbonyl. The term "aminoalkyl" refers to both secondary and tertiary amines wherein the alkyl or substituted alkyl groups may be either same or different and the point of attachment is on the nitrogen atom. The term "halogen" is defined as Cl, Br, F, and I.

Pharmaceutically acceptable salts can be formed of these antiprogestin compounds from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from inorganic bases, preferably alkali metal salts, for example, sodium, lithium, or potassium, and organic bases, such as ammonium, mono-, di-, and trimethylammonium, mono-, di- and triethylammonium, mono-, di- and tripropylammonium (iso and normal), ethyl-dimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2- methylpiperidinium, mono-, di- and triethanolammonium, ethyl diethanolammonium, n-butylmonoethanolammonium, tris(hydroxymethyl)methylammonium, phenylmonoethanolammonium, and the like.

The antiprogestin compounds of this invention were prepared according to the following schemes from commercially available starting materials or starting materials which can be prepared using literature procedures. These schemes show the preparation of representative antiprogestin compounds of this invention.

Scheme 1

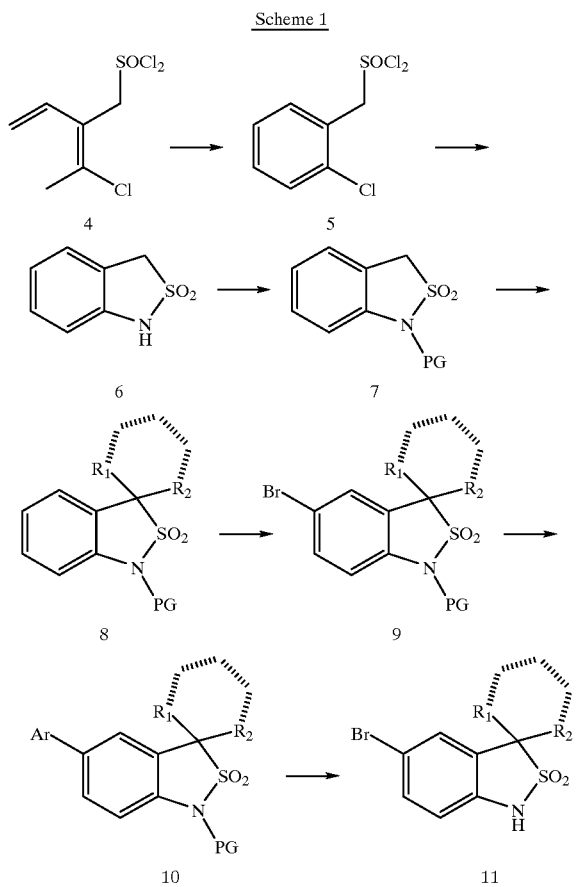

According to Scheme 1, commercially available sulfonyl chloride 4 is converted via the sulfonamide 5 to the 2,1-benzisothiazoline 2,2-dioxide 6 as described in the literature (Chiarino et al, *J. Heterocycl. Chem.* 23(6), 1645–9, 1986). The nitrogen atom of sultam 6 is then protected by a suitable protecting group, e.g., trimethyl silyl ethyl.

The protected sultam 7 next is treated with a strong organo-metallic base (e.g., butyl lithium, lithium diisopropylamide, potassium hexamethyldisilylazide) in an inert solvent (e.g., THF, diethyl ether) under nitrogen at reduced temperature (ca. −20° C.) (Kende et al, *Synth. Commun.* 12, 1, 1982). The resulting di-anion then is treated with excess electrophile such as an alkyl halide, preferably the iodide. If $R_1$ and $R_2$ are to be joined such as the product contains a spirocycle at position 3, then the electrophile should be bifunctional, i.e., a diiodide. Subsequent bromination of the sultam 8 proceeds regioselectively at room temperature with bromine in acetic acid (an organic co-solvent such as dichloromethane may be added as required) in the presence of sodium acetate, to give the aryl bromide 9. Judicious choice of reaction conditions may facilitate simultaneous removal of the protecting group at this step.

The bromide 9 then is reacted with a palladium salt (e.g., tetrakis(triphenylphosphine)palladium(0)), in a suitable solvent (e.g., THF, dimethoxyethane, ethanol, toluene) under an inert atmosphere (argon, nitrogen). The mixture then is treated with an arylboronic acid or arylboronic acid ester and a base (sodium carbonate, triethylamine, potassium phosphate) in water or fluoride source (cesium fluoride) under anhydrous conditions at elevated temperature to give the biphenyl sultam 10. Finally, the protecting group is removed under appropriate conditions and the final product 11 is isolated and purified by standard means.

If $R_1$ and $R_2$ are different then the intermediate is prepared by reacting the dianion of 7 with one equivalent of the electrophile $R_1$—X (X=leaving group, e.g., iodide). The resultant mono-alkylated compound may be then isolated and re-subjected to the reaction conditions using $R_2$—X, or alternatively used in situ for the second alkylation with $R_2$—X. Alternatively, if the desired product is to contain $R_2$=H, then the isolated mono-alkylated intermediate is taken though the subsequent steps.

Scheme 2

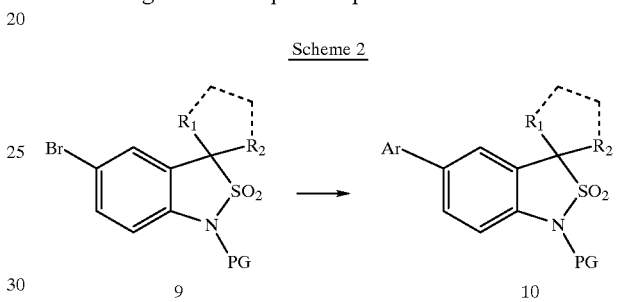

Other methodologies also are available for coupling the aryl group, Ar, to the sultam platform: for example, reaction of the bromide 9 with an aryl stannane, aryl zinc, or aryl magnesium halide in the presence of a palladium or nickel catalyst (Scheme 2). The required aryl-metallic species are formed via standard techniques. Furthermore, the bromide 9 may be converted to an aryl boronic acid via standard procedures (treatment with n-butyllithium followed by addition of trimethyl borate and subsequent boronic ester hydrolysis) that will then undergo the range of previously described coupling procedures with a suitable aryl bromide.

The antiprogestational activity of the compounds of this invention was demonstrated in an in vitro standard pharmacological test procedure which evaluated the antiprogestational potency of a representative compound of this invention by measuring its effect on PRE-luciferase reporter activity in CV-1 cells co-transfected with human PR and PRE-luciferase plasmids. When evaluated in the above-described test procedure, the compound of Example 1 had an $IC_{50}$ of 900 nM. The $IC_{50}$ is the concentration of test compound that gives half-maximal decrease in 3 nM progesterone induced PRE-luciferase activity.

The results obtained in this standard pharmacological test procedure demonstrate that the compounds of this invention are progestational antagonists, and are therefore useful as oral contraceptives (male and female), in hormone replacement therapy (particularly when combined with an estrogen), in the treatment of endometriosis, luteal phase defects, benign breast and prostatic diseases and prostatic, breast, ovarian, uterine and endometrial cancers.

The antiprogestin compounds of this invention can be used alone as a sole therapeutic agent or can be used in combination with other agents, such as other estrogens, progestins, or androgens.

The antiprogestational compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.02 $\mu$g/kg–750 $\mu$g/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

The following provides the preparation of a representative compound of this invention.

EXAMPLE 1

5-(3-chlorophenyl)spiro[2,1-benzisothiazole-3(1H), 1'-cyclohexane] 2,2-dioxide

To 1,3-dihydro-2,1-benzisothiazoline 2,2-dioxide (Chiarino et al, *J. Heterocycl. Chem.* 23(6), 1645–9, 1986) (0.74 g, 4.4 mmol) in anhydrous dichloromethane (minimum amount) at room temperature was added sequentially N,N-diisopropylethylamine (0.76 mL, 4.4 mmol) and 2-(trimethylsilyl)ethoxymethyl chloride (0.77 mL, 4.4 mmol). After 30 min, the reaction was poured into water (50 mL), the layers were separated, and the aqueous phase was extracted with ethyl acetate (2×50 mL). The organic layers were combined, washed with brine (30 mL), dried over magnesium sulfate, filtered and concentrated in vacuo to give 1,3-dihydro-1-(2'-trimethylsilylethyl)-2,1-benzisothiazoline 2,2-dioxide (1.3 g, 99%) as an off-white solid. $^1$H NMR (CDCl$_3$, 300 MHz) $\delta$0.02 (s, 9 H), 0.97 (dd, 2 H, J=8.3, 8.2 Hz), 3.73 (dd, 2 H, J=8.2, 8.3 Hz), 4.40 (s, 2 H), 5.08 (s, 2 H), 7.05 (d, 1 H, J=7.4 Hz), 7.07 (dd, 1 H), 7.26 (d, 1 H, J=7.4 Hz), 7.35 ('t', 1 H, J=7.6, 7.6 Hz). MS ((+) APCI m/z 317[M+NH$_4$]$^+$.

To 1,3-dihydro-1-(2'-trimethylsilylethyl)-2,1-benzisothiazoline 2,2-dioxide (1.3 g, 4.3 mmol) in anhydrous tetrahydrofuran (13 mL) at room temperature was added 1,5-diiodopentane (1.29 mL, 8.6 mmol). The mixture was cooled to −78° C. and lithium bis(trimethylsilyl)amide (1.0 M solution in tetrahydrofuran, 17.3 mL, 17 mmol) was added. After 15 min, the reaction mixture was poured into water (50 mL), the layers were separated, and the aqueous phase was extracted with ethyl acetate (3×50 mL). The organic layers were combined, washed with brine (30 mL), dried over magnesium sulfate, filtered and concentrated in vacuo. Purification by flash column chromatography (5% ethyl acetate/hexane) on silica gel gave 1,3-dihydro-3-spirocyclohexyl-1-(2'-trimethylsilylethyl)-2,1- benzisothiazoline 2,2-dioxide (0.8 g, 51%) as an off-white solid. $^1$H NMR(CDCl$_3$, 300 MHz) δ0.00 (s, 9 H), 0.95 (dd, 2 H, J=8.3, 8.2 Hz), 1.18–2.36 (m, 10 H), 3.72 (dd, 2 H, J=8.2, 8.3 Hz), 5.06 (s, 2 H), 7.03 ('t', 1 H, J=7.8 Hz), 7.06 (dd, 1 H, J=1, 7.6 Hz), 7.18 (dd, 1 H, J=1.1, 7.6 Hz), 7.28 (dt, 1 H, J=1.3, 7.7 Hz). MS (EI) m/z 367[M]$^+$.

To a stirred solution of 1,3-dihydro-3-spirocyclohexyl-1-(2'-trimethylsilylethyl)-2,1-benzisothiazoline 2,2-dioxide (0.8 g, 2.2 mmol) in glacial acetic acid (5 mL) at room temperature was added dropwise a solution of bromine (0.11 mL, 2.2 mmol) in glacial acetic acid (2.2 mL) After stirring for 10 min, anhydrous sodium acetate (0.18 g, 2.2 mmol) was added and the solution was concentrated in vacuo. The residue was dissolved in ethyl ether (50 mL) and washed sequentially with water (50 mL), aqueous saturated sodium bicarbonate solution (50 mL), water (50 mL) and brine (30 mL). The organic layer was dried over magnesium sulfate, filtered and concentrated in vacuo. Purification by flash column chromatography (20% ethyl acetate/hexane) on silica gel gave a complex mixture of products (0.56 g) with identical TLC characteristics as a white foam. The mixture was used without further purification.

A solution of the mixture containing 5-bromo-1,3-dihydro-3-spirocyclohexyl-1-(2'-trimethylsilylethyl)-2,1-benzisothiazoline 2,2-dioxide (0.56 g, 1.25 mmol) and tetrakis(triphenylphosphine)palladium(0) (100 mg) in toluene (25 mL) was stirred under a flow of nitrogen for 25 min. To the solution was added sequentially solutions of 3-chlorophenylboronic acid (0.4 g, 2.5 mmol) in absolute ethanol (5 mL) and potassium carbonate (0.35 g, 2.5 mmol) in water (5 mL). The mixture was heated to 80° C. for 16 h and allowed to cool. The reaction mixture was poured into aqueous saturated sodium bicarbonate solution (50 mL) and the layers were separated. The aqueous phase was extracted with ethyl acetate (3×50 mL). The organic layers were combined, washed with water (50 mL) and brine (30 mL) and dried over magnesium sulfate. The solution was filtered, concentrated in vacuo, and the residue was purified by flash column chromatography on silica gel (2% ethyl acetate/toluene) and then by HPLC to give the title compound (65 mg) as a low melting yellow foam. HPLC conditions: Zorbax PRO, C18, 10u, 15A, 50×250 mm; mobile phase composition and gradient program, 70% water/30% AcCN; flow rate, 100 mL/min; injection volume, 120 mg/3 mL MeOH; detection wavelength, 280 nm, 500 PSI; temperature, amb. $^1$H NMR (DMSO-d$_6$, 300 MHz), δ1.47–2.19 (m, 10 H), 6.87 (d, 1 H, J=8.2 Hz), 7.38 ('d', 1 H, J=8.1 Hz), 7.46 ('t', 1 H, J=7.9, 7.7 Hz), 7.56 (dd, 1 H, J=1.7, 8.2 Hz), 7.62 ('d', 1 H, J=7.7 Hz), 7.71, ('d', 1 H, J=1.7 Hz), 7.75 (bs, 1H), 10.55 (bs, 1 H). MS (EI) m/z 347[M]$^+$. Anal. Calcd for C$_{18}$H$_{18}$ClNO$_2$S: C, 62.15; H, 5.22; N, 4.03. Found: C, 59.84; H, 5.30; N, 3.57.

EXAMPLE 2

Biological Activity

The antiprogestational activity of the compound of Example 1 was demonstrated in a conventional pharmacological test.

Reagents

Growth medium: DMEM (Bio Whittaker) containing 10% (v/v) fetal bovine serum (heat inactivated), 0.1 mM MEM non-essential amino acids, 100 U/ml penicillin, 100 mg/ml streptomycin, and 2 mM GlutaMax (GIBCO, BRL).

Experimental medium: DMEM (Bio Whittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

Test Procedure

Stock CV-1 cells were maintained in growth medium. Co-transfection was done using 1.2×10$^7$ cells, 5 mg pLEM plasmid with hPR-B inserted at Sph1 and BamH1 sites, 10 mg pGL3 plasmid with two PREs upstream of the luciferase sequence, and 50 mg sonicated calf thymus DNA as carrier DNA in 250 ml. Electroporation was carried out at 260 V and 1,000 mF in a Biorad Gene Pulser II. After electroporation, cells were resuspended in growth medium and plated in 96-well plate at 40,000 cells/well in 200 ml. Following overnight incubation, the medium was changed to experimental medium. Cells were then treated with reference or test compounds in experimental medium. Compounds were tested for antiprogestational activity in the presence of 3 nM progesterone. Twenty-four hours after treatment, the medium were discarded, cells were washed three times with D-PBS (GIBCO, BRL). Fifty ml of cell lysis buffer (Promega, Madison, Wis.) was added to each well and the plates were shaken for 15 min in a Titer Plate Shaker (Lab Line Instrument, Inc.). Luciferase activity was measured using luciferase reagents from Promega.

When evaluated in the above-described test procedure, the compound of Example 1 had an IC$_{50}$ of 900 nM. The IC$_{50}$ is the concentration of test compound that gives half-maximal decrease in 3 nM progesterone induced PRE-luciferase activity.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed:

1. A method of contraception which comprises administering to a female of child bearing age for 28 consecutive days:

a) a first phase of from 14 to 24 daily dosage units of a progestational agent equal in progestational activity to about 35 to about 100μg levonorgestrel;

b) a second phase of from 1 to 11 daily dosage units, at a daily dosage of from about 2 to 50 mg, of an antiprogestin compound of Formula 1:

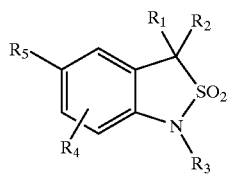

wherein

R$_1$ and R$_2$ are each, independently, selected from the group consisting of hydrogen, alkyl, substituted alkyl, hydroxy, alkoxy, substituted alkoxy, aryl, substituted aryl, heteroaryl, substituted heteroaryl, arylalkyl, heteroarylalkyl, and alkynyl; or R$_1$ and R$_2$ are taken together form a ring and together contain —CH$_2$(CH$_2$)$_n$CH$_2$—, —CH$_2$CH$_2$CMe$_2$CH$_2$CH$_2$—, —O(CH$_2$)$_p$CH$_2$—, —O(CH$_2$)$_q$O—, —CH$_2$CH$_2$OCH$_2$CH$_2$—, —CH$_2$CH$_2$NR$_7$CH$_2$CH$_2$—; or R$_1$ and R$_2$ are a double bond, said double bond having two methyl groups bonded to the terminal end, having a cycloalkyl group bonded to the terminal end, having an oxygen bonded to the terminal end, or having a cycloether bonded to the terminal end;

$R_7$ is hydrogen or an alkyl having 1–6 carbon atoms;

n=1–5;

p=1–4;

q=1–4;

$R_3$ is hydrogen, hydroxyl, $NH_2$, alkyl, substituted alkyl, alkenyl, alkynyl, substituted alkynyl or $COR^A$;

$R^A$ is hydrogen, alkyl, substituted alkyl, alkoxy, substituted alkoxy, aminoalkyl, or substituted aminoalkyl;

$R_4$ is hydrogen, halogen, —CN, alkyl, substituted alkyl, alkoxy, or substituted alkoxy;

$R_5$ is selected from the group consisting of (i) and (ii):

(i) a substituted phenyl ring having the structure,

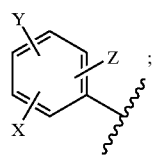

X is halogen, OH, —CN, alkyl, substituted alkyl, alkoxy, substituted alkoxy, thioalkyl, substituted thioalkyl, S(O)alkyl, S(O)$_2$alkyl, aminoalkyl, substituted aminoalkyl, —NO$_2$, perfluoroalkyl, 5 or 6 membered heterocyclic ring containing in its backbone 1 to 3 heteroatoms, thioalkoxy, —COR$^B$, —OCOR$^B$, or —NR$^C$COR$^B$;

$R^B$ is hydrogen, alkyl, substituted alkyl, aryl, substituted aryl, alkoxy, substituted alkoxy, aminoalkyl, or substituted aminoalkyl;

$R^C$ is hydrogen, alkyl, or substituted alkyl;

Y and Z are each, independently, hydrogen, halogen, —CN, —NO$_2$, alkoxy, alkyl, or thioalkyl; and (ii) a five or six membered heteroaryl ring containing in its backbone 1, 2, or 3 heteroatoms selected from the group consisting of O, S, SO, SO$_2$ and NR$^6$ with said ring carbons being optionally substituted with one or two substituents independently selected from the group consisting of hydrogen, halogen, CN, NO$_2$, alkyl, alkoxy, aminoalkyl, COR$^D$, and NR$^E$COR$^D$;

$R^D$ is hydrogen, alkyl, substituted alkyl, aryl, substituted aryl, alkoxy, substituted alkoxy, aminoalkyl, or substituted aminoalkyl;

$R^E$ is hydrogen, alkyl, or substituted alkyl;

$R^6$ is hydrogen, alkyl, alkoxycarbonyl, or is absent when the nitrogen of NR$^6$ is bonded to a ring double bond;

or pharmaceutically acceptable salt thereof; and c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

2. The method according to claim 1 wherein the progestational agent is levonorgestrel and wherein:

$R_1$ and $R_2$ are taken together form a ring and together contain —CH$_2$(CH$_2$)$_n$CH$_2$—;

n=2–3;

$R_3$ is hydrogen;

$R_4$ is hydrogen;

$R_5$ is (iii) or (iv):

(iii) the substituted phenyl ring (i) wherein:

X is halogen, OH, —CN, alkyl, alkoxy, thioalkyl, substituted thioalkyl, S(O)alkyl, S(O)$_2$alkyl, aminoalkyl, substituted aminoalkyl, —NO$_2$, perfluoroalkyl, 5 or 6 membered heterocyclic ring containing in its backbone 1 to 3 heteroatoms, or thioalkoxy; or (iv) the five or six membered heteroaryl ring (ii) containing in its backbone 1, 2, or 3 heteroatoms selected from the group consisting of O, S, and NR$^6$ with said ring carbons being optionally substituted with one or two substituents independently selected from the group consisting of hydrogen, halogen, CN, NO$_2$, alkyl, and alkoxy.

3. The method according to claim 1 wherein the progestational agent is levonorgestrel and wherein:

$R_5$ is (v) or (vi):

(v) the substituted phenyl ring (i) having the structure,

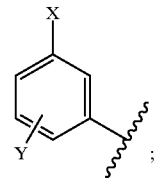

X is halogen, —CN, or —NO$_2$;

Y is hydrogen, halogen, —CN, —NO$_2$, alkoxy, alkyl, or thioalkyl; or (vi) the five or six membered heteroaryl ring containing in its backbone a heteroatom selected from the group consisting of O, S, and NR$^6$ with said ring carbons being optionally substituted with one or two substituents independently selected from the group consisting of hydrogen, alkyl halogen, CN, and NO$_2$;

$R^6$ is hydrogen, or is absent when the nitrogen of NR$^6$ is bonded to a ring double bond.

4. The method according to claim 1 in which the antiprogestin compound is 5-(3-chlorophenyl)-spiro[2,1-benzisothiazole-3(1H),1'-cyclohexane]2,2-dioxide or a pharmaceutically acceptable salt thereof.

5. The method according to claim 1 wherein the progestational agent is selected from the group consisting of levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, and (17-deacetyl) norgestimate.

6. The method according to claim 1 which comprises administering to a female of child bearing age consecutively over a 28 day cycle:

a) a first phase of 21 daily dosage units of a progestational agent equal in progestational activity to about 35 to about 100 µg levonorgestrel;

b) a second phase of 3 daily dosage units of an antiprogestin compound of formula 1, each daily dosage unit containing an antiprogestin compound at a daily dosage of from about 2 to 50 mg; and c) optionally, 4 daily dosage units of an orally and pharmaceutically acceptable placebo to be administered on each day of the 28-day cycle following the first phase and second phase.

7. The method according to claim 1, wherein $R_5$ is the phenyl ring (i), wherein said phenyl ring is substituted with —CN and halogen groups, and wherein said halogen is a fluorine atom.

8. The method according to claim 1, wherein $R_5$ is the heteroaryl ring (ii) and is a thiophene group.

9. The method according to claim 8, wherein said thiophene group is substituted with one —CN group.

10. The method according to claim 8, wherein said thiophene group is substituted with one methyl group.

* * * * *